United States Patent [19]

Dragner et al.

[11] Patent Number: 5,498,315
[45] Date of Patent: Mar. 12, 1996

[54] METHOD OF MODIFYING THE OPACITY OF PAPER AND PAPER PRODUCED THEREBY

[75] Inventors: Louis R. Dragner; Bernard F. North, both of Rock Hill, S.C.

[73] Assignee: Sequa Chemicals, Inc., Chester, S.C.

[21] Appl. No.: 439,950

[22] Filed: May 12, 1995

Related U.S. Application Data

[62] Division of Ser. No. 265,402, Jun. 24, 1994.

[51] Int. Cl.⁶ .................... D21H 17/07; D21H 17/00; D21H 17/21
[52] U.S. Cl. .................... 162/164.6; 162/164.7; 162/166; 162/167; 162/168.1; 162/179
[58] Field of Search .................... 162/158, 164.6, 162/164.7, 168.1, 166, 167, 179

[56] References Cited

U.S. PATENT DOCUMENTS

| | | | |
|---|---|---|---|
| 2,772,967 | 12/1956 | Padbury et al. | 92/3 |
| 2,772,969 | 12/1956 | Reynolds, Jr. et al. | 162/179 |
| 3,141,787 | 7/1964 | Goetze et al. | 106/252 |
| 3,619,356 | 11/1971 | Keen | 162/162 |
| 3,981,990 | 9/1976 | Kelly et al. | 424/78 |
| 4,032,473 | 6/1977 | Berg et al. | 252/358 |
| 4,060,507 | 11/1977 | Floyd et al. | 260/21 |
| 4,376,078 | 3/1983 | Töpfl | 162/164.6 |
| 5,292,363 | 3/1994 | Hutcheson | 106/243 |
| 5,296,024 | 3/1994 | Hutcheson | 106/243 |

*Primary Examiner*—David L. Lacey
*Assistant Examiner*—Jose Fortuna
*Attorney, Agent, or Firm*—Mitchell D. Bittman

[57] ABSTRACT

A method of enhancing the opacity of paper and paper of enhanced opaqueness is provided wherein a reaction product of dimerized acid and alkanol diamine an further including a surfactant, is added to a slurry of cellulose fibers in a papermaking process. A viscosity controlling gent may be added to the reaction product.

13 Claims, No Drawings

5,498,315

METHOD OF MODIFYING THE OPACITY OF PAPER AND PAPER PRODUCED THEREBY

This is a division of application Ser. No. 08/265,402, filed June 24, 1994.

FIELD OF THE INVENTION

This invention relates to compositions for use in the papermaking process, a papermaking process employing the compositions to add opaqueness to the paper, and a paper produced using the compositions.

BACKGROUND OF THE INVENTION

The quality of paper produced from cellulose fibers (i.e. wood pulp or the paper produced by the recycling of paper made from wood pulp) is often judged by its opacity. Paper producers have long sought to improve these vital characteristics so that an enhanced paper may be obtained.

This and other desired characteristics have been obtained in the past by supplying the pulp slurry of cellulose fibers or furnish with additives prior to the slurry entering the papermaking machine. Various additives are well known in the art. For example, titanium dioxide powder is known to be an excellent whitener. Titanium dioxide, however, is among the most expensive materials that may be added to the slurry. Thus, despite the effectiveness of such material as a brightener, its use is limited and satisfactory replacements have been needed.

Kaolin clay has also been used as a filler in paper to improve brightness in the ultimate product. Generally, the kaolin clay is calcined and then suspended in an aqueous solution prior to being added to the furnish. The clay must be continuously agitated prior to entering the slurry or the solid particles begin to form sediment at the bottoms of the clay holding tanks. Although kaolin clay provides brightness, as well as opacity to the finished paper product, the relative difficulty of adding it to the slurry results in a less than excellent additive.

When clay is added to the pulp slurry, the slurry needs additional chemicals. A retention aid is necessary to retain the clay in the sheet, which will add extra cost to the sheet. Adding clay to the slurry will also have an adverse effect on drying the sheet of paper. The paper maker will slow the paper machine down to maximize the drying to make sure the sheet is dried, which will increase the cost of the sheet. The clay also increases wear on the paper machine. This wear shows up in shorter life for some of the pans of the paper machine. The wire, felt, doctor blade and refiners especially, show wear when clay is used. With the increased abrasiveness of the clay down time is longer and more frequent.

Hydrated aluminum silicate has also been employed as a clay substitute in the papermaking process. It has properties similar to kaolin clay and, thus, results in the same disadvantages when used to make paper.

Many compositions have been added to the slurry in an attempt to size the paper, i.e. render the paper water repellent. Most known sizes, such as those disclosed in U.S. Pat. No. 2,142,986 to Arnold, Jr. and U.S. Pat. No. 3,096,232 to Chapman, employ a type of wax. For example, Arnold, Jr. discloses that an emulsion of wax in a solution of deacetylated chitin, paraffin waxes, Japan wax, carnauba wax, higher aliphatic alcohols, or synthetic waxes may be employed as the waterproofing agent in a sizing composition. A softening agent such as aliphatic alcohols containing 12 to 20 carbons is also present in the composition of Arnold, Jr. Chapman discloses the use of paraffin waxes or water-insoluble derivatives of resins for producing aqueous wax emulsions with cationic modified starches.

In U.S. Pat. Nos. 5,296,024 and 5,292,363 a papermaking composition is disclosed for enhancing opaqueness comprising the reaction product of fatty acid and diamine. This composition is effective although further improvements are desired for strength of the paper, and coefficient of friction.

SUMMARY OF THE INVENTION

It is an object of the present invention to provide a composition for adding to paper during the papermaking process so that the resulting paper has enhanced characteristics.

It is another object of the present invention to provide a composition that adds opacity to paper to which it is added.

Still another object of the present invention is to provide a composition for adding to the pulp slurry of cellulose fibers to enhance opacity without adversely affecting other paper properties.

Still another object of the present invention is to provide a process wherein a composition is added to recycled pulp of cellulose fibers to form a paper having desirable physical characteristics.

Still another object of the present invention is to provide a process for adding a composition to pulp slurry of cellulose fibers in the papermaking process that will result in a paper having enhanced opacity.

Yet another object of the present invention is to provide a paper having the desirable characteristic of enhanced opacity.

Generally speaking, the present invention is directed to a composition used as an additive to the pulp slurry of cellulose fibers from which paper is formed, the process of making paper from the additive-containing slurry, and the paper made according to that process. The composition contains the reaction product of dimerized acid and alkanol amine, wherein the composition further includes a surfactant. A viscosity controlling agent may be added to the composition as necessary or desired; an acid may be added to adjust pH; and a defoamer may be added if needed to control foam. In a further embodiment the composition contains the reaction product of dimerized acid, alkanol amine and a fatty acid.

DETAILED DESCRIPTION

The composition is added to the pulp slurry after the wood pulp has been bleached to remove lignin and other undesirables and de-inked, if recycled paper pulp is being used, but before the pulp enters into the headbox of a papermaking machine. The composition may be added alone, or in conjunction with other brighteners, opacifying agents, and sizes. For example, in one embodiment of the invention, the composition hereof may be added in conjunction with papermaking clays such as kaolin, or in conjunction with a brightness and opacifying agent based on the stearic acid diamide of amino ethyl ethanolamine.

The composition may be added to any pulp slurry to obtain the desired physical characteristics and is especially useful for enhancing the characteristics of paper made from the recycled pulp of cellulose fibers. The amount of composition, as well as the mounts of each component in the composition, will vary depending on the characteristics and types of pulp slurry to which the composition is added. As is well known, different sources of wood pulp have different peculiarities that attribute to their ability to be brightened, made more opaque and more water resistant, and easily processed. For instance, some wood pulp requires a higher concentration of brightening and opacifying agents than others to produce a finished paper product having identical characteristics.

The composition employed in the present invention comprises the reaction product formed from the reaction of dimerized acid and alkanol amine and wherein the composition further includes a surfactant. This composition provides an increase in opacity to the paper produced and gives an improved paper strength and coefficient of friction. This composition is also more efficient, i.e. effective at lower dosages, than an opacifying agent based on the stearic acid diamide of amino ethyl ethanolamine.

A dimerized acid is where a molecule of an unsaturated acid is reacted with another to form a dicarboxylic acid with a molecular weight approximately the sum of these acids and generally is the product of a modified Diels-Alder reaction of unsaturated acids. The final product can be a mixture of dimer, trimer, and higher compounds. Generally the dimerized acids useful herein will have from 18 to 54 carbons, preferably 21 to 40 carbons. Typically the dimer acid will have the following properties: an acid value of 170–270; a color (Gardner) of 6–18; a viscosity at 25° C. of 5000–10,000 cst; and a Sap value of 170–202. Suitable dimer acids include dimers of poly unsaturated acids such as those derived from tall oil, soybean oil, palm oil, etc. or from available poly unsaturated acids such as linoleic acid, linolenic acid, eleostearic acid, etc. and mixed dimers from above described poly unsaturated acid with mono-unsaturated acids such as oleic acid, propenoic acid, 2 methyl propenoic acid, butenoic acid, octadecenoic acid, etc. The preferred dimerized acids are dimerized tall oil acid, dimerized soybean oil acids and liquid mono cyclic $C_{21}$ dicarboxylic acid.

The alkanol amines that are useful include the monoamines, as well as the diamines and triamines. Suitable alkanol amines include: monoethanol amine, diethanol amine, amino ethyl ethanol amine, dimethyl amino propyl amine, and dimethyl amino ethyl amine and mixtures of these amines. The preferred amine is amino ethyl ethanol amine as it gives improved opacity to the treated paper. Dimes, including ethylene diamine, diethylene triamine, and higher analogues can also be used with the alkanol amine to make a higher molecular weight reaction products which have the advantage of providing improved brightness, and strength to the treated paper.

In a further embodiment of this invention the composition will comprise the reaction product of the dimerized acid, alkanol amine and a fatty acid. This is generally carried out by either reacting the dimerized acid with the alkanol amine then the fatty acid or by reacting the fatty acid with the alkanol amine and then the dimerized acid. The fatty acid preferably is a long chain fatty acid having between 12 and 18 carbons. Suitable fatty acids include lauric acid, myristic acid, iso-stearic and palmitic acid with the preferred acid being stearic acid. The fatty acids can also include the hydroxy substituted and/or the unsaturated fatty acids including ricinoleic acid, oleic acid, linoleic acid and eleostearic acid.

The reaction product will generally comprise of from 60 to 85% by weight, preferably 66–84%, of dimerized acid and 15 to 40% by weight, preferably 16–34% of alkanol amine. In the further embodiment the reaction product will generally comprise from 50 to 30% by weight, preferably 55 to 35% of dimerized acid, 30 to 10% by weight, preferably 20 to 15% of alkanol amine and 20 to 50%, preferably 25 to 45 of fatty acid. This reaction product base is then emulsified with a surfactant. Generally the composition comprises the following, by weight: 2–35%, preferably 7–30%, of the reaction product base; optionally 1 to 15%, preferably 2–10%, of an inorganic or organic acid; optionally 0.1 to 2%, preferably 0.2–1%, of a salt; 0.1–5%, preferably 0.2–1%, of a surfactant; and 45–97%, preferably 70–90%, of water.

The reaction product can be prepared as follows. The dimer acid is charged to a rosin flask equipped with an electric stirrer, condenser, and a nitrogen sparge tube. The dimer acid is heated to 70° C. to 130° C., preferably above 100° C. The amine is added slowly using an addition funnel. The exotherm can be controlled by the addition rate. When the amine charge is complete, the batch is heated up. At 150° C. to 180° C., water of reaction starts to distill out. Distillation will be complete at 220° C. A small amount of defoamer maybe added to help control the foaming, if needed. When the theoretical amount of water is collected, a sample is taken for an acid value. If the acid value is less than 5, the batch is cooled. If acid value is greater than 5 cooking is continued until the acid value is less than 5. The reaction product can then be emulsified by heating water in a reaction vessel to 75° C. to 98° C. and charging surfactant, acid and salt. The molten reaction product base is then poured in at rate to keep the temperature below the boiling point. After the base is charged, the emulsion is left to stir at 90° C. for 30 minutes, then cooled.

This emulsion is added to paper pulp in the wet end of a paper machine generally at a rate of 40 to 200 pounds per ton of paper. The finished paper will show an increase in opacity, while not having an adverse effect on other paper properties including brightness, strength, and coefficient of friction (CoF). The interest in paper opacity is to reduce the amount of inorganic filler added. This is increasingly important with the increased use of recycled paper. The inorganic fillers reduce the speed of the paper machine and they also are abrasive, which adds wear and tear on the machine.

The type of pulp slurry to which the composition may be added is unimportant. In fact, the make-up of the composition may be varied depending on the type of cellulose fibers from which the pulp slurry is made. To increase opaqueness, additional amounts of the composition may be employed. In addition, the use of pulp which has been recycled from papers may require other adjustments to the composition, particularly when the recycled pulp is dark or otherwise discolored. All such adjustments to the composition may be easily made by one of ordinary skill in the art according to the invention disclosed herein.

The pulp to which the composition is added is made into a slurry using conventional techniques. After formation, the slurry is stored in holding tanks or fed to a papermaking machine, such as a Fourdrinier machine, in a conventional manner. The pulp may be bleached to remove unwanted pollutants such as lignins and de-inked if pulp made from recycled paper is used. The papermaking composition disclosed herein may be added either to the slurry when it is in the holding tank or may be added to the slurry as it moves along to the headbox of the papermaking machine. Preferably, the composition is applied to the pulp in the holding tank before it travels to the headbox.

When the slurry containing the composition reaches the headbox of the papermaking machine, paper is formed therefrom using conventional papermaking techniques and materials. The paper produced according to the present invention exhibits excellent characteristics of opaqueness.

In a further embodiment of the present invention, other materials may be added in conjunction with the composition. For instance, kaolin clay may be added in addition to the inventive composition so that the paper made therefrom exhibits increased opaqueness. Other additives which are well known in the an may also be added in conjunction with the composition disclosed herein.

In addition, it is preferred that the particle size of the composition be as small as possible. It is highly desirable that the papers produced according to the present invention have substantially uniform opaqueness over its entire surface. Smaller particle sizes aid in the dispersibility of the particles within the slurry so that the desired characteristics are uniform throughout the paper. These smaller particle sizes may be obtained by either homogenizing the product in a high speed mixer or by rapidly cooling the composition from the high temperature at which the reaction product base is formed as described herein.

Ethoxylated surfactant can be used to emulsify the base. Suitable surfactants or combinations of surfactants including the following may be used: stearyl amine with from 2 to 20 moles of ethylene oxide; coconut amine with from 2 to 20 moles of ethylene oxide; tallow amine with from 2 to 20 moles of ethylene oxide; or any other ethylene oxide adduct of a fatty amine. The surfactant further contributes to the desired dispersability of the reaction product in the water emulsion. If the amount of surfactant added is excessive, the sizing capability of the composition will be adversely affected. In the absence of a surfactant, the paper may be of a poor quality due to the decreased dispersibility of the composition, which results in spots or specks on the paper indicating a lack of dispersibility.

A weak acid is preferred to disperse the reaction product. The acid maintains an acidic pH preferably within the range of from about 4 to about 5 during the making of the composition. The acid acts as a catalyst by creating an acidic environment wherein the cationic softener base exhibits increased reactivity. Inorganic acids and/or organic acids of the following type maybe used to prepare the salt of the product to help stabilize the emulsion: hydrochloric acid, sulfuric acid, phosphoric acid, acetic acid, propanoic acid, etc. Weak organic acids such as acetic acid or formic acid are especially preferred in the composition. Strong acids, of course, may be used to control the pH, but cost and safety considerations may restrict their use.

Preferably, a viscosity controlling agent such as a salt is added during production of the papermaking composition. Generally, the sodium salts and potassium salts are known viscosity controlling agents including sodium propionate, sodium acetate, potassium propionate, potassium acetate, sodium chloride, potassium chloride. Preferred salts include sodium acetate and sodium chloride. This component may be deleted, but the processing time for creating the composition may be substantially increased.

The present invention may be better understood by reference to the following examples.

Example I 368 grams of a tall oil dimerized acid (83% dimer acid, 15.5% trimer acid, 1.5% monomer acid) was charged to a liter resin flask. The nitrogen sparge was set on low. The dimer acid was then heated to 1000° C. and 132 grams of amino ethyl ethanol amine was charged over 10 minutes. The batch was slowly heated to 200° C. The batch was held at 200° C. for an hour and the acid value was checked. It was less than 5. The batch was cooled to 125° C. While the batch was cooling, to a 2 liter resin flask the following items were charged: 40 grams of 84% acetic acid, 12 grams of CAM 2 POE (coconut amine with 2 moles ethylene oxide), 1 gram of potassium acetate and 1000 grams of water. The mixture under agitation was heated to 80° C., and the reaction product base at 125° C. was slowly poured in. The solution was held at 90° C. for thirty minutes and cooling was started. Adjustments were made, and the final solution was a 30% non-volatile solids and clear amber.

Example II 419 grams of a tall oil dimerized acid (83% dimerized acid, 1.5% monomer, 15.5% trimer) was charged following the same procedure as in Example I. Then 37 grams of diethylene triamine and 44 grams of monoethanol amine were charged. The final product was cooled to room temperature. It was an amber viscous liquid with an acid number of 2.7 and an amine number of 41. To 265 grams of water was charged 0.8 grams of TAM 15 POE (tallow amine, 15 moles ethylene oxide), 2.2 grams of 84% acetic acid, 0.5 grams of 25% sodium hydroxide and 33 grams of the reaction product base. The solution was hated to 90° C. and held for 30 minutes. The while milky emulsion was cooled down and the solids were adjusted to 11%.

Example III 737 grams of a tall oil 95% dimer acid (95% dimer acid, 4% trimer acid and 1% monomer acid) and 264 grams of amino ethyl ethanol amine were charged and the same procedure was followed as Example I. The emulsion was prepared same as the emulsion in Example II. It was adjusted to 10% non-volatile solids with a milky white emulsion.

Example IV 375 grams of a tall oil dimerized acid (60% trimer acid and 40% dimer acid) was charged to a 2 liter round bottom flask. The contents of the flask were heated to 90° C. and 125 grams of amino ethyl ethanol amine was charged. The temperature was allowed to exotherm to 130° C. during the amine charge. The batch was heated to 180° C. and the distillate collected. When the acid value was less than 5, then batch was cooled down and put in a can. 15 grams of base, 265 grams of water, 5 grams of 84% acetic acid, 0.7 grams of SAM 5 POE (stearyl amine with 5 moles ethylene oxide) and 0.25 grams of potassium hydroxide were heated to 90° C. and held for 30 minutes. The milky white emulsion was adjusted to 5% non-volatile solids.

Example V 369 grams of a tall oil dimerized acid (83% dimer acid, 1.5% monomer acid and 15.5% trimer acid) was charged with 98 grams of amino ethyl ethanol amino and 33 gms of dimethyl amino propylamine. The same procedure was used as Example I. The emulsion was prepared as in Example II.

Example VI

To 396 grams of a tall oil dimerized acid (83% dimer acid, 1.5% monomer acid, 15.5% trimer acid) was added 36 grams diethylene diamine and 68 grams of amino ethyl ethanol amine. The same procedure was followed as described in Example I. 33 grams of base was charged to 260 grams of water, 1 gram of TAM 15 POE (tallow amine with 15 moles ethylene oxide) and 10 grams of 84% acetic acid. The emulsion prepared as in Example II made a milky white emulsion.

Example VII 331 grams of dimer acid (reaction product of linoleic acid and acrylic acid) was reacted with 169 grams of amino ethyl ethanol amine. The same procedure as described in Example I was used to emulsify the viscous product.

Example VIII

The emulsions of the reaction product prepared in Examples I, II and IV were tested by preparing hand sheets 8×8 inches by adding the following amounts of the Example I, II and IV samples to a furnish containing the wood pulp. These samples were compared against a blank and against a Comparative sample containing the stearic acid diamide of amino ethyl ethanolamine (see U.S. Pat. No. 5,296,024). The sheets after pressing at 40 psig to squeeze out water are dried at 240° F., then conditioned (TAPPI standard T402 OM-88), then calendared at 150° F. and 600 psi.

The hand sheets were tested as follows: brightness and opacity were measured on a Technobrite instrument with an average of five readings being taken; the Mullen-Burst test measuring strength were run according to TAPPI standard T403 OM-85; the Scott Bond internal bond strength was measured on a Scott Bond tester; the tear resistance was measured on an Elmendorf tester according to TAPPI procedure T414/OM-88; and the CoF (coefficient of friction) was measured by a slide angle tester Model TMI 3225. The hand sheets were tested with the following results.

| Recycled Pulp (gms) | 60 | 60 | 60 | 60 | 60 | 60 | 60 | 60 | 60 |
|---|---|---|---|---|---|---|---|---|---|
| Comparative (gms) |  | 4 | 8 |  |  |  |  |  |  |
| Example I (gms) |  |  |  | 4 | 8 |  |  |  |  |
| Example II (gms) |  |  |  |  |  | 4 | 8 |  |  |
| Example IV (gms) |  |  |  |  |  |  |  | 4 | 8 |
|  |  |  | Test Results |  |  |  |  |  |  |
| Brightness | 57.0 | 57.7 | 57.0 | 53.5 | 52.1 | 55.0 | 53.8 | 54.3 | 53.7 |
| Opacity (TAPPI) | 95.5 | 94.5 | 96.6 | 97.7 | 97.8 | 95.9 | 97.1 | 96.6 | 97.1 |
| Mullen Burst | 7.8 | 5.1 | 3.3 | 4.0 | 4.0 | 5.0 | 5.0 | 7.0 | 6.3 |
| CoF | 21.5 | 19.0 | 19.0 | 20.5 | 23.5 | 22.0 | 22.5 | 21.5 | 22.5 |
| Scott bond | 45.0 | 32.4 | 28.8 | 33.5 | 37.5 | 33.0 | 38.5 | 38.7 | 37.8 |

All of the sheets of paper made from the Example I, II and IV samples have higher opacity than the pulp. The sheets prepared from the Examples samples all had higher CoF than the Comparative sample. In addition, the sheets produced with the Examples samples had strength properties which were not diminished as in the Comparative sample.

Example IX

All of the reaction product bases prepared in Example I thru VII were viscous liquids with the following properties:

|  | Acid Number | Amine Number | Color Gardner |
|---|---|---|---|
| Example I | 2.0 | 141.0 | 10 |
| Example II | 2.7 | 41.0 | 11 |
| Example III | 1.2 | 149.0 | 6 |
| Example IV | 1.0 | 123.0 | 13 |
| Example V | 3.8 | 112.6 | 10 |
| Example VI | 1.3 | 101.0 | 13 |
| Example VII | 3.7 | 174.3 | 14 |

The emulsions of the reaction products of Examples I thru VII were tested as described in Example VIII at a level of 13.2 dry pounds of sample per ton of paper product with the following test results.

|  | Blank | #1 | #2 | #3 | #4 | #5 | #6 | #7 |
|---|---|---|---|---|---|---|---|---|
| Pulp (gms) | 60 | 60 | 60 | 60 | 60 | 60 | 60 | 60 |
| Example I (gms) |  | 4 |  |  |  |  |  |  |
| Example II (gms) |  |  | 4 |  |  |  |  |  |
| Example III (gms) |  |  |  | 4 |  |  |  |  |
| Example IV (gms) |  |  |  |  | 4 |  |  |  |
| Example V (gms) |  |  |  |  |  | 4 |  |  |
| Example VI (gms) |  |  |  |  |  |  | 4 |  |
| Example VII (gms) |  |  |  |  |  |  |  | 4 |
|  |  | Test Results |  |  |  |  |  |  |
| Brightness | 57.0 | 53.5 | 55.0 | 54.2 | 54.3 | 54.1 | 53.0 | 54.8 |

-continued

|  | Blank | #1 | #2 | #3 | #4 | #5 | #6 | #7 |
|---|---|---|---|---|---|---|---|---|
| Opacity (TAPPI) | 95.5 | 97.7 | 95.9 | 97.0 | 96.6 | 97.0 | 96.4 | 95.5 |
| Opacity (ISO) | 91.9 | 95.5 | 92.2 | 94.3 | 93.5 | 94.3 | 92.9 | 92.3 |
| Mullen | 7.8 | 4.0 | 5.0 | 6.2 | 7.0 | 6.4 | 6.0 | 4.5 |
| Scott Bond | 45.0 | 33.5 | 33.0 | 37.0 | 38.7 | 37.3 | 38.4 | 31.0 |
| Tear | 50.4 | 45.6 | 43.2 | 52.8 | 40.8 | 40.8 | 36.8 | 39.9 |
| CoF | 21.5 | 20.5 | 22.0 | 22.0 | 21.5 | 21.5 | 21.5 | 21.0 |

The emulsions of the reaction product were then tested at level of 26.4 dry pounds of sample per ton of paper product with the following test results.

|  | Blank | #1 | #2 | #3 | #4 | #5 | #6 | #8 |
|---|---|---|---|---|---|---|---|---|
| Pulp (gms) | 60 | 60 | 60 | 60 | 60 | 60 | 60 | 60 |
| Example I (gms) |  | 8 |  |  |  |  |  |  |
| Example II (gms) |  |  | 8 |  |  |  |  |  |
| Example III (gms) |  |  |  | 8 |  |  |  |  |
| Example IV (gms) |  |  |  |  | 8 |  |  |  |
| Example V (gms) |  |  |  |  |  | 8 |  |  |
| Example VI (gms) |  |  |  |  |  |  | 8 |  |
| Example VII (gms) |  |  |  |  |  |  |  | 8 |

|  | Blank | #1 | #2 | #3 | #4 | #5 | #6 | #7 |
|---|---|---|---|---|---|---|---|---|
| Brightness | 57.0 | 52.1 | 53.8 | 52.9 | 53.7 | 53.1 | 52.1 | 53.1 |
| Opacity (TAPPI) | 95.5 | 97.8 | 97.1 | 97.2 | 97.1 | 96.8 | 97.1 | 96.8 |
| Opacity (ISO) | 91.9 | 95.6 | 94.2 | 94.6 | 94.4 | 93.8 | 94.3 | 92.5 |
| Mullen | 7.8 | 4.0 | 5.0 | 5.0 | 6.3 | 5.2 | 6.3 | 5.9 |
| Scott Bond | 45.0 | 37.5 | 38.3 | 37.0 | 37.8 | 35.9 | 37.7 | 38.0 |
| Tear | 50.4 | 41.6 | 52.0 | 48.8 | 43.2 | 44.8 | 27.6 | 39.8 |
| CoF | 21.5 | 23.5 | 22.5 | 22.0 | 22.5 | 22.0 | 22.5 | 21.5 |

The above results show the opacity of the paper is greatly increased with the addition of the organic opacity agent.

Example X

To a reaction vessel equipped with a heating source and an agitator 273 grams of dimer acid (83% dimer, 15.5% trimer acid and 0.5% monomer acid) was charged. The acid was heated to 100° C. under an inert atmosphere and 97 grams of amino ethyl aminoethanol was slowly charged. The temperature was maintained at less than 110° C. during the charge. The batch was slowly heated to 200° C. The temperature was held at 200° C. for an hour and the acid value 2.8 mg of KOH per gram sample was measured. At that point 130 grams of 70% stearic acid and 30% palmitic acid was charged. The temperature was maintained at 200° C. for one and half hours. A sample was drawn, the acid value was checked on the sample and it was less than 5.0 mg of KOH per gram of sample. The heating source was removed from the reaction vessel, and the batch was allowed to cool to 90° C. The tan solid melted at 40° C., had an acid value of 4.4 mg of KOH per gram of sample, and an amine value of 59 mg of KOH per gram of sample.

The product prepared a white emulsion using the procedure as described in Example I.

Example XI

To a suitable reaction vessel was charged 237 grams of 70% stearic acid and 30% palmitic acid. The acid was heated to 100° C. with, a nitrogen blanket during the heat up cycle. To the acid, 89 grams of amino ethyl amino ethanol was charged. The temperature was maintained below 110° C. during the charge. The batch was heated to 200° C. At 200° C., the acid value was checked and is 3.0 mg of KOH per gram of sample. 175 grams of dimer acid (83% dimer acid, 15.5% trimer acid, and 1.5% monomer acid) was charged.

The temperature was maintained at 200° C. for four hours until the acid value was less than 5.0. The batch was allowed to cool to 90° C. The light tan solid melted at 55° C. It had an acid value of 2.8 mg of KOH per gram of sample and an amine number of 31.6 mg of KOH per gram of sample.

The tan solid was emulsified using the procedure described in Example I and was tested as described in Example VIII versus the blank and the same Comparative Sample.

|  | 1 | 2 | 3 | 4 |
|---|---|---|---|---|
| Virgin Pulp | 60 | 60 | 60 | 60 |
| Retention aid | 0.5 | 0.5 | 0.5 | 0.5 |
| Comparative | — | 8.0 | — | — |
| Example XI | — | — | 4.0 | 8.0 |
| Test Results |  |  |  |  |
| Brightness | 53.0 | 54.3 | 53.8 | 55.1 |
| Opacity | 96.3 | 97.0 | 96.8 | 96.7 |
| Mullen Burst | 6.4 | 4.3 | 6.0 | 6.2 |
| Tensile | 3.0 | 2.8 | 3.9 | 3.5 |

These Example XI samples show an increase in opacity and brightness making a stronger sheet with Mullen Burst and tensile equivalent to the untreated paper. The Comparative sheet is weaker than the Example XI sheets.

What is claimed is:

1. A method of producing a paper with enhanced opacity comprising the steps of:
   providing a pulp slurry of cellulose fibers;
   adding to said slurry a composition wherein said composition comprises the reaction products formed from the reaction of a dimerized acid and an alkanol amine and wherein said composition further includes a surfactant; and forming said slurry into said paper.

2. The method as defined in claim 1 wherein said dimerized acid has a carbon chain length of 18 to 54 carbons.

3. The method as defined in claim 1 wherein the composition comprises the reaction product of said dimerized acid, said alkanol amine and a fatty acid.

4. The method as defined in claim 1 wherein said composition further comprises adding a viscosity controlling agent.

5. The method as defined in claim 4 wherein said viscosity controlling agent is selected from the group consisting of sodium acetate and sodium chloride and said surfactant is an ethoxylated surfactant.

6. The method as defined in claim 1 wherein said surfactant is present in said composition in an amount of at least 0.2% by weight.

7. The method as defined in claim 1 further comprising the step of adding kaolin clay to said slurry.

8. The method as defined in claim 1 wherein said composition is added to said slurry at a level of 40 to 200 pounds per ton of paper.

9. In a paper product made from cellulose fibers the improvement comprising, said product having an opacity enhancing composition therein comprising the reaction products formed from the reaction of a dimerized acid and an alkanol amine and wherein said composition further comprises a surfactant.

10. The paper product as defined in claim 9 wherein said surfactant is an ethoxylated surfactant.

11. The paper product as defined in claim 9 wherein said dimerized acid has a carbon chain length of 18 to 54 carbons.

12. The paper product as defined in claim 9 wherein the composition comprises the reaction products of said dimerized acid, said alkanol amine and a fatty acid.

13. The paper product as defined in claim 9 wherein said reaction product is present in said composition in an amount of at least 7 to 30% by weight and said surfactant is present in an amount of 0.2% to 1% by weight.

* * * * *